United States Patent [19]

Schmielau

[11] Patent Number: 5,534,953
[45] Date of Patent: Jul. 9, 1996

[54] TRAINING DEVICE FOR THE THERAPY OF PATIENTS HAVING PERCEPTION DEFECTS

[76] Inventor: Fritz Schmielau, Schonbockener Strasse 30B, 23556 Lubeck, Germany

[21] Appl. No.: 269,697

[22] Filed: Jul. 1, 1994

[51] Int. Cl.$^6$ .............................. A61B 3/00; A61B 3/02
[52] U.S. Cl. .............................. 351/203; 351/226
[58] Field of Search ........................ 351/200, 203, 351/224, 226

[56] References Cited

U.S. PATENT DOCUMENTS

| 4,611,583 | 9/1986 | Wasserman | 351/226 |
| 4,804,262 | 2/1989 | Katsuhiko et al. | 351/226 |

FOREIGN PATENT DOCUMENTS

| 0242723 | 10/1987 | European Pat. Off. |
| 85/02102 | 5/1985 | WIPO |
| 91/07908 | 6/1991 | WIPO |

*Primary Examiner*—William L. Sikes
*Assistant Examiner*—Huy Mai
*Attorney, Agent, or Firm*—Merchant, Gould, Smith, Edell, Welter & Schmidt

[57] ABSTRACT

A training device for the therapy of, in particular, brain-damaged patients having perception defects, includes a large number of signalers (6) arranged on one surface (4) for the production of perceptual stimuli, a marking element that is firmly attached in a specific location on the surface (4) and on which the patient must focus his eyes during the therapy, a start-signaling device (16) for producing a starting signal, a control mechanism (20), a reaction-detecting device (22), and a time-determining device (24).

23 Claims, 2 Drawing Sheets

TRAINING DEVICE FOR THE THERAPY OF PATIENTS HAVING PERCEPTION DEFECTS

BACKGROUND OF THE INVENTION

The invention relates to a training device for the therapy of—in particular, brain-damaged—patients having perception defects.

In neuropsychology there is an ever-increasing need, not only for comprehensive diagnostics, but also for suitable therapy of perception defects. This concerns especially patients who have vision defects, primarily after a stroke. It is important that many test results are interpreted as accurately as possible and that therapeutic measures are offered at an appropriate level.

The high time requirements of the diagnostics and therapy performed until now are to be considered especially critical for ordinary clinical practice. Because of frequently increased fatigue of the patients, the use of automatically operating, computer-supported devices—familiar until now—for the perimetric measurement of the visual field was considered unsuitable, especially for application with brain-damaged persons.

Also, compensatory procedures have been proposed that include, for instance, the training of saccadic eye movements in the anopic field of vision. After initial reports about successes and a subsequently failed replication, this method has no longer been pursued in the last few years.

SUMMARY OF THE INVENTION

Therefore, it is the task of this invention to create a training device for the therapy of—in particular, brain-damaged—patients having perception defects that makes effective therapy of perception defects possible in a simple manner.

This problem is solved with a device of the type mentioned in the beginning that is characterized according to the invention by —a plurality of signalers, arranged on a surface, for producing perceptual stimuli;

—a marking element to be firmly placed on a specific—in particular, central—location on the surface, on which the patient has to focus his eyes during the therapy;

—a signal initiator for producing a starting signal;

—a control device that activates the start initiator at the beginning of an operating cycle; selects and activates, for a specific period of time, a single signaler or a signaler group, after expiration of the first time interval, which is randomized between specific predetermined limits; and—after expiration of the second time interval after the activation of the selected signaler or the selected signaler group—initiates a subsequent operating cycle in which the operating time is shorter than the second time interval;

—a reaction-detecting device for recording the reaction of the patient on the activation of the selected signaler or the selected signaler group by the control device; and —a time-determining device, which measures the reaction time of the patient between the time of the activation of the selected signaler or the selected signaler group and the time of the reaction of the patient registered by the reaction-detecting device, whereby the control device repeats the activation of the same signaler or signaler group in the next operating cycle, or in one of the subsequent operating cycles, if the reaction time measured by the time-determining device is shorter than a predetermined minimum or longer than a predetermined maximum that is shorter than the second time interval, or if the reaction registered by the reaction-detecting device is wrong according to a selection criterion entered beforehand.

The device according to the invention makes possible an effective and specific training with the goal of functional recovery of perceptual performances. Above all, patients with partial visual defects or injuries of auditory functions—which can occur as a consequence of a brain infarct (stroke), a brain hemorrhage, or a cranio-cerebral trauma—can profit from the device according to the invention.

Accurate determination of the defective areas of the perceptual field is a prerequisite for work with the training device according to the invention. For this purpose, usually a conventional perimeter is used for the visual modality with, as a rule, a higher precision in the central visual field only.

For the subsequent work with the present device according to the invention—with which the determined defect areas of the perceptual field should be "trained away"—it is not only uncritical, but even desirable, that the attention of the patient to be treated is drawn to the location of the areas, within his perceptual field, that were determined to be defective and in need of training, and to the type of signaler configuration to which a specific reaction is desired. Thereby, namely, the patient is put in a position to be better able to concentrate on the defective areas and partial functions—which is an indispensable precondition for effective training.

To be able to carry out the training in the entire perceptual field, a plurality of signalers is arranged on a surface whose expansion is calculated in such a way that the entire perceptual field of the patient in therapy is covered when the patient focuses his eyes on a specific spot on the surface. This spot contains a marking element and should preferably lie approximately in the center of the surface.

The training device according to the invention operates in successively occurring operating cycles, controlled by a controlling device, whereby a specific, selected signaler or a specific, selected signaler group is activated in each operating cycle. At the beginning of each operating cycle, the control device activates a start initiator which, thereupon, emits a starting signal. This starting signal—which is, preferably, associated with a sensory modality other than the sensory modality to be trained—should give the patient the instruction that a new operating cycle is commencing. Thus, the starting serves, as it were, as a warning signal, which should increase the attention of the patient.

Before a specific individual signaler or a specific signaler group is selected and activated by the control device, the control device—after activating the start initiator—first of all, allows a first time interval to pass that is randomly selected within specific predetermined limits—that means it is selected with a different duration within predetermined limits, from operating cycle to operating cycle, according to the principle of randomization—so the patient cannot prepare himself for fixed switching times of the signaler or signaler group.

After the activation of the selected signaler or the selected signaler group, it is determined whether and how the patient reacts to the perceptual stimulus produced thereby; for this purpose, a reaction-detecting device according to the invention is provided that detects the occurrence, the performance, and the type of the reaction.

Furthermore, the device according to the invention contains a time-determining device that measures the reaction time of the patient between the time of the activation of the selected signaler or the selected signaler group and the time of the reaction of the patient recorded by the reaction-detecting device.

This arrangement is especially important for the device according to the invention in order to distinguish whether the area of the perceptual field of the patient that corresponds to the location of the selected signaler or the selected signaler group functions normally, or to what degree it is damaged, or whether the perceptual performance was improved by the training with the device according to the invention, so that further training at this location is no longer necessary, or whether the training has to be repeated and, thus, intensified, in that area of the visual field because the reaction of the patient was absent, too late, or wrong.

For this purpose, the control device according to the invention is programmed in such a way that it repeats—in the next operating cycle or in one of the subsequent operating cycles—the activation of the same signaler or the same signaler group if the reaction time measured by the time-determining device is either shorter than a predetermined minimum or longer than a predetermined maximum—which is shorter than the second time interval—and/or if the reaction-detecting device classifies the type of reaction as wrong.

If the reaction time lies below the minimum, it has to be assumed that the reaction of the patient is based on chance and, thus, has to be ignored as incorrect. However, if no reaction has been determined within the maximal predetermined time, this state is assessed as "without reaction," with the result that a severely damaged area in the perceptual field has to be assumed as still in need of more intensive training for rehabilitation.

In the latter case, the same signaler, the same signaler group, an immediately adjacent signaler, or an immediately adjacent signaler group is then repeatedly activated in one or several of the subsequent operating cycles so that the defective area is trained intensively. If, after successful conclusion of the training, the defective area of the perceptual field is sufficiently or completely rehabilitated, the training is continued in another, still defective, area of the perceptual field by repeated presentation of the appropriately coordinated signaler or signaler group.

By this kind of iterative procedure, the training device according to the invention obtains adaptive qualities while it automatically intensifies the training in the defective areas of the perceptual field, whereby an especially effective training can be realized with the goal of as quick a functional restitution of the perceptual-field defects as possible.

It is especially advantageous if, during several consecutive operating cycles, the control device selects and activates specific signalers or subassemblies of signalers associated with the boundary area between a healthy and a defective area of the perceptual field of the patient to be treated, in a specific sequence, according to which signalers or signaler groups would be activated successively in the direction from the healthy area to the defective area.

If the reaction of the patient is classified as wrong and/or the reaction time does not lie within the previously mentioned ranges, the signalers or signaler groups can, optionally, also be activated again in the direction from the defective area to the healthy area.

With that kind of iterative procedure, a reduction of the defective area can be attained especially effectively. By the iterative training, the boundary between the healthy area and the defective area is gradually shifted in the direction of the defective area.

An especially simple construction of the reaction-detecting device can be realized in that a push-button switch is provided that the patient needs to actuate when he perceives the selected signaler or signaler group.

Advisedly, the marking element has a sensor that is connected to the control device and recognizes whether the patient is focusing his eyes on the marking element or not; in the latter case, the control device interrupts the operation of the device until the patient directs his eyes to the marking element again. In this manner, errors during the training because the eyes were not focused on the marking element are basically stopped.

To increase the comfort during the therapy with the device according to the invention—which ultimately also has a positive effect on the patient's power of concentration—a support is provided for the head of the patient. In order that the training can be carried out with the same intensity on all locations of the perceptual field up to the periphery, the signalers should be distributed over the surface in a basically homogeneous density and, preferably, also arranged at equal distances from each other.

An especially favorable geometry results when the surface, with the signalers arranged on it, is developed in the shape of a spherical section—and, in particular, a hemispherical form—whereby the head of the patient to be treated is basically positioned with the eyes at the center of the sphere. The distance between the signalers and the organs of perception of the patient, whose head is steady in the head support, should preferably be larger than the arm length of the patient. Here, optionally, an average arm length can be assumed.

In a presently especially preferred embodiment, the signalers consist of preferably dot-shaped light sources for producing optical signals that, optionally, also have different colors and/or are arranged in a specific configuration—for instance, along a variably oriented line. However, alternatively, it is also conceivable to develop the signalers as sound transducers for producing audible signals, to be able to determine and train auditory perceptivity.

To the control device can be coupled a memory in which an algorithm for the automatic presentation of individual signalers or signaler groups can be stored. To the control device can also be coupled an input device by which the signalers can optionally also be selected manually by the operator and, thus, be addressed selectively.

Other preferred embodiments of the invention are indicated in the subclaims.

BRIEF DESCRIPTION OF THE DRAWINGS

In the following, a preferred embodiment of the invention is described using the enclosed drawings.

Shown are.

DETAILED DESCRIPTION OF THE PREFERRED EMBODIMENTS

Figure 1:
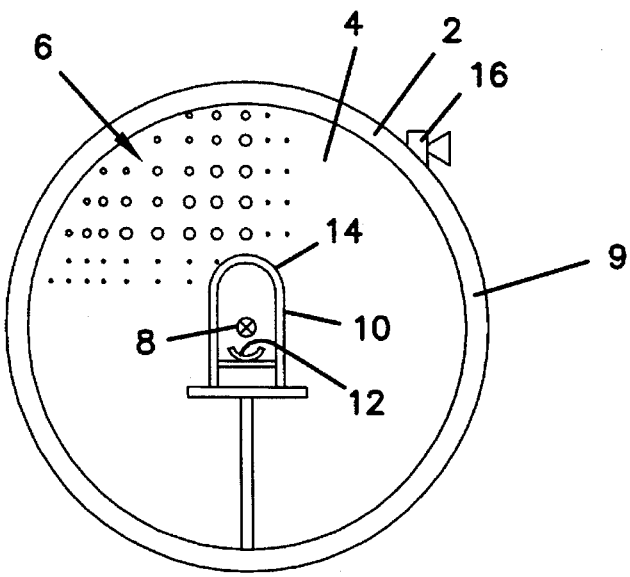
FIG. 1 A top view on a part of the device according to the invention.
Figure 2:
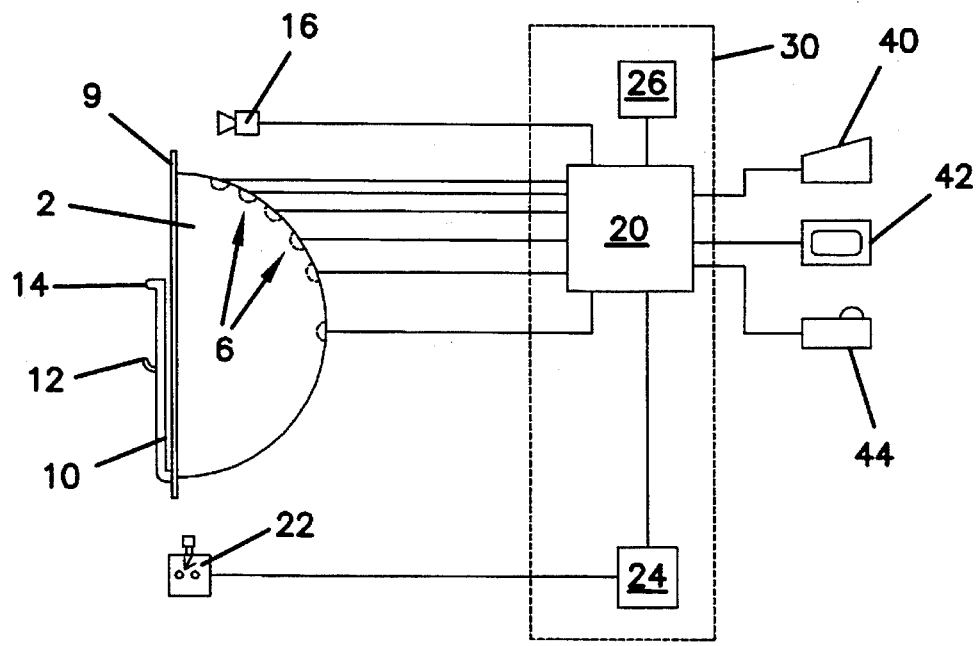
FIG. 2 A block diagram of the device.
Figure 4:
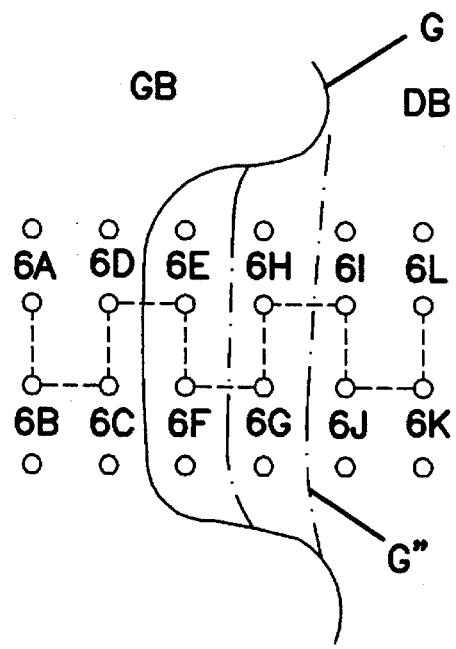
FIG. 4 A cut-out from the light-source field, with a schematic representation of the mode of operation of a preferred embodiment of the device.

As FIGS. 1 and 2 reveal, the represented training device for achieving a functional restitution of perception defects has a hemisphere on whose inner surface (4) a plurality of light sources (6) are arranged. In FIG. 4, which shows an interior view on the inner surface (4), the light sources (6) are represented on only a part of surface (4), for reasons of clarity; however, they are actually distributed over the surface (4) in a basically homogeneous density and, preferably, arranged so they lie on hyperbola lines.

With as high a density of light sources (6) as possible up to the edge of the surface (4)—and, thus, in the periphery of the perceptual field—an especially effective training can be carried out with the goal of a functional restitution of defects of the perceptual field.

Preferably, the light sources (6) are developed as luminous diodes. But it is nevertheless also possible to use other light sources or to develop apertures in the surface (4)—for instance, instead of the light sources—and to attach the ends of photoconductors there.

At this place, it should also be pointed out that the invention is not limited to the represented hemisphere, but that the surface carrying the light sources can also have another shape; for instance, it can be flat.

Furthermore, it is conceivable to treat auditory perception defects, instead of visual perception defects, with the device at issue. In this case, audible sound transducers have to be used instead of the light sources (6). For this application, it could be beneficial to carry out the training in a basically closed, sound-muffled housing at whose inner surface the audible signalers are arranged; a housing of that type could also consist, for instance, of a hemisphere or a complete sphere.

In the center of the surface (4) is fastened a marking element (8) on which the patient has to focus his eyes during the therapy. In the marking element a sensor is contained which recognizes whether the patient is actually focusing his eyes on the marking element or not, and which emits corresponding signals.

Usually the hemisphere (2) is placed on a frame in such a way that the plane formed by peripheral edge (9) basically extends vertically. The frame is not represented in the figures.

A head support (10), which has a dish-shaped chin rest (12) and a bow-shaped forehead strap (14), is attached to the hemisphere (2) and/or the (not represented) frame. The head support (10) with the chin rest and the forehead strap (14) is arranged in such a way that the patient is situated with his eyes at approximately the center of a sphere—of which the hemisphere (2) is a part—and looks into the interior of the hemisphere (2) at the surface (4) with the light sources (6) and, in doing so, he can focus his eyes on the marking element (8) if he places his chin on the chin support and contacts the forehead strap (14) with his forehead.

Accordingly, the head support (10) is placed in the plane described by the peripheral edge (9) of the hemisphere (2), or in the immediate vicinity of the same. Generally, the distance of the light sources (6) from the eyes of the patient whose head is steady on the head support (1) is not smaller than the arm length of the patient.

Moreover, an audible signaler (16) is attached to the hemisphere (2), as FIG. 1 reveals.

FIG. 2 represents a block diagram with the essential components of the training device. The device shows a control mechanism (20) to which the light sources (6) are connected. For reasons of clarity, also in FIG. 2 only some of the light sources (6), with their lines leading to the control mechanism (20), are represented. In addition, the sensor in the marking element (8) and the audible signaler (16) are connected to the control mechanism (20).

Furthermore, a push-button switch (22) is provided that is placed close to the patient. However, it can also be provided loose, on a cable. During the therapy, the patient always actuates the push-button switch (22) when he perceives the light of a light source (6) or of a configuration of light sources. The push-button switch (22) is connected to a time-determining device (24) that, in turn, communicates with the control mechanism (20) by way of a conduit.

Alternately, also a push-button selector switch or several push-button switches can be provided, which makes possible a differentiated determination of the reaction of the patient with respect to the recognition of differently oriented configurations of light sources.

To the control mechanism (20) is also coupled a memory (26) in which, for instance, an algorithm can be stored for the operation of the control mechanism (20). Usually the control mechanism (20), the time-determining device (24), and the memory (26) are contained in a microcomputer (30), which is schematically indicated with an interrupted line, in FIG. 2, as a block.

For the input of data and for manually influencing the operation of the control mechanism (20), a keyboard is connected to the latter in the represented embodiment. A monitor (42) and a printer (44) are connected to the control mechanism (20) for the output of data and operational results.

In the following, the mode of operation of the described device will be explained—in particular, using FIG. 3 and 4.

Before the start of the therapy of the patient with the training device, the defective areas of the perceptual field must first be accurately determined, which usually takes place with conventional perimeters. Once the location and intensity of the defects in the perceptual field are known, the training with the device commences. For this purpose, the patient has to hold his head steady on the head support (10) in the manner described before, while advisedly being seated on a chair in as relaxed a position as possible.

Moreover, the patient is informed about the location, type, and intensity of the defects in his perceptual field, the area to be trained, and/or the partial visual function so he can concentrate especially on those areas and partial visual functions during the training, whereby the training can be furthered.

The training is carried out in successive operating cycles that are controlled by the control mechanism (20). At the beginning of each operating cycle, the control mechanism (20) briefly activates the audible signaler (16) so the latter emits an audible warning signal whereby the beginning of this operating cycle is indicated to the patient.

Figure 3:
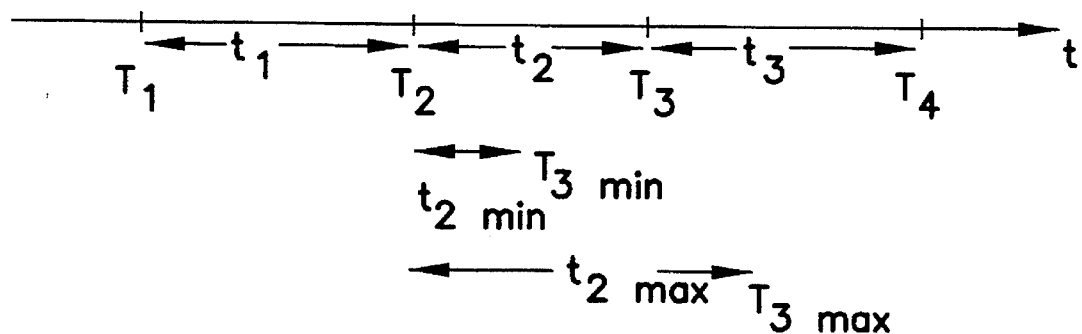
FIG. 3 A time diagram that represents the mode of operation of the device.

According to the time diagrams shown in FIG. 3, the operating cycle starts at $T_1$. A first time interval $t_1$, which is randomized within specific predetermined limits, passes subsequently. That means the time interval $t_1$ is changeable from operating cycle to operating cycle according to the principle of randomization. Only after expiration of the randomized first time interval $t_1$ are the light sources (6) activated.

The reason for the randomized first time interval $t_1$ is that the patient cannot grow accustomed to a fixed time lapse after the sound of audible signaler (12), but is, as it were, "surprised" by the light source activated at that moment. Only that way can reasonable results be achieved.

After expiration of the first time interval $t_1$, the control mechanism (20) either selects a single light source or a group of light sources and activates it at a time $t_2$. An algorithm stored in the memory (26) determines which light source (6) or group of light sources is selected. However, it is also possible to interrupt or de-activate the algorithm and, instead, to selectively activate a specific light source (6) or group of light sources manually by way of the keyboard (40).

After the selected light source or group of light sources has lit up, the patient is asked to signal—by actuation, or not, of the push-button switch (22)—whether or not he perceived the light stimulus, or—in case of a choice—which configuration he recognized. If he perceived the light stimulus, he presses the push-button switch (22).

This happens at time $T_3$, after expiration of a certain delay time $t_2$, after the selective light source or group of light sources is switched on at time $T_2$. The reaction of the patient by pressing the push-button switch (22), though, must take place within a delay time $t_2$ that is longer than a predetermined minimum $t_{2\ min}$ and smaller than a predetermined maximum $t_{2\ max}$.

If the patient presses the push-button switch (22) already at $t_2 < t_{2\ min}$, this has to be a chance occurrence because the value of $t_{2\ min}$ is designed for the shortest possible reaction time of the person. In that case, the result is evaluated as negative by the control mechanism (20). If, on the contrary, the patient presses the push-button switch (22) after expiration of a delay time $t_2 > t_{2\ max}$, or if the patient does not react at all, the result is also evaluated as negative by the control mechanism (20).

In the two "negative" cases mentioned above, the control mechanism (20) makes the decision to repeat the activation of the same light source or group of light sources in a subsequent operating cycle as in the present operating cycle, or to activate another immediately adjacent light source or group of light sources. This procedure is carried out during subsequent operating cycles until the patient recognizes a light stimulus of the corresponding light source or group of light sources.

During the trial operation of the device according to the invention, it became apparent that the number of those procedures during one session cannot be arbitrarily high, because the power of concentration of the patient is limited; however, with that kind of iterative procedure over several sessions, it was possible to reduce the defects in the perceptual field.

If, in case of a choice, the patient presses the wrong push-button switch, the control mechanism (20) makes a decision whether, in a subsequent operating cycle, the same or another configuration of light sources is activated in the same area of the visual field. If the correct push-button switch is actuated, the same or another group of light sources with the same or another configuration of light sources is activated in a subsequent operating cycle.

The device is freely programmable by the control mechanism (20) with respect to the selection of the light sources (6). Therefore, different algorithms can be used, after which the control mechanism (20) activates the light sources (6) in different sequences and patterns, one after another.

The same counts as well for the manner of repetition. It is conceivable, for instance, to always activate the same light source or group of light sources, or to iteratively always go through a certain sequence of light sources or groups of light sources until the defect in the perceptual field is "trained away."

A preferred algorithm is represented in FIG. 4. Here the control mechanism (20) selects, during several operating cycles, light sources (6A to 6K) that are located in an area between a healthy region GB and a defective region DB of the perceptual field of the patient to be treated.

The control mechanism (20) consecutively activates the represented selected light sources (6A to 6L), in a "meandering" sequence, in such a way that the light sources are successively activated in the direction from the healthy range GB into the defective range DB and, therefore, the light stimuli "run" from the healthy area GB into the defective area.

Thus, first the light sources (6A to 6T) in the healthy range GB are activated consecutively and, subsequently, the light sources (6E to 6L) are activated consecutively in the defective range DB. This sequence, lasting over twelve operating cycles, is repeated until the boundary G between the healthy area GB and the defective area DB shifts in the direction of the defective area DB and the defective area DB is, consequently, reduced.

By this example, to which the invention is not necessarily restricted, the principle of the training device according to the invention can be clearly recognized, according to which—after repeated "tentative impressions" in the defective area DB—the latter is ultimately "trained away" and, therefore, reduced.

However, effective training is achieved only when the patient continuously focuses his eyes on the marking element (8) during the session (compare FIG. 1 and 2). Should this not be the case, the sensor contained in the marking element (8) transmits a corresponding signal to the control unit (20), which thereupon interrupts the operation until the patient directs his eyes again to the marking element (8). Optionally, also a warning signal is sounded by way of the audible signal (16).

Moreover, as is apparent from FIG. 3, a second delay time $t_3$ follows at time $T_3$, before the next operating cycle is initiated at $T_4$. The second delay time $t_3$ can optionally be adjusted so it is variable and randomizable.

The training results can be indicated on the monitor (42) and printed by way of the printer (44). Furthermore, it is possible to statistically evaluate the training results. In conclusion, it should be pointed out that, for some applications, it could be advantageous to produce light stimuli of different colors and to also control the brightness of the light.

I claim:

1. Training device for the therapy of, in particular, brain-damaged patients having perception defects, comprising:

—a large number of signalers arranged on one surface for the production of perceptual stimuli;

—a marking element that is firmly attached in a specific—and, in particular, central—location on the surface and on which the patient must focus his eyes during the therapy;

—a start-signaling device for producing a starting signal;

—a control mechanism that activates a start-signaling device at the beginning $T_1$ of an operating cycle; selects and activates a single signaler or a signaler group after the expiration of a first time interval $t_1$, randomized within specific predetermined limits; and initiates a subsequent operating cycle, after expiration of a second interval $(t_2+t_3)$ following the time $T_2$ of the activation of the selected signaler or the selected signaler group, whereby the duration of the activation is shorter than the second time interval;

—a reaction-detecting device for detecting the reaction of the patient to the activation of the selected signaler or the selected signaler group by the control mechanism; and —a time-determining device that measures the reaction time $t_2$ of the patient between the time $T_2$ of the activation of the selected signaler or the selected signal group and the time $T_3$ of the patient's reaction recorded by the reaction-detecting device, whereby the control mechanism repeats the activation of the same signaler or signaler group and/or an immediately adjacent signaler or an immediately adjacent signaler group in the next operating cycle, or in one of the subsequent operating cycles, if the reaction time $t_2$ measured by the time-determining device is shorter than a predetermined minimum $t_{2\ min}$ in or longer than a predetermined maximum $t_{2\ max}$—which is shorter than the second time interval—or when the reaction of the patient detected by the reaction-detecting device is wrong according to a selection criterion keyed in beforehand.

2. Device according to claim 1, wherein, during several consecutive operating cycles, the control mechanism selects and activates specific signalers or (6A to 6L) or signaler groups associated with the border area between a healthy and a defective area (GB, DB) of the perceptual field of the patient in therapy.

3. Device according to claim 2, wherein the control mechanism selects and activates the signalers (6A to 6L) or signaler groups in a specific sequence, after which the signalers (6A to 6L) or signaler groups are successively activated in the direction from the healthy area (GB) into the defective area (DB).

4. Device according to at least claim 3, wherein the reaction-detecting device has one or several push-button switches that have to be pressed by the patient if he perceives the selected signaler or the selected signaler group.

5. Device according to claim 4, wherein the second time interval $t_3$ is variable and, optionally, randomizable.

6. Device according to claims 5, wherein the marking element has a sensor that is connected to the control mechanism and recognizes whether the patient fixes his eyes on the marking element or not, whereby, in the latter case, the control mechanism interrupts the operation of the device until the patient has again fixed his eyes on the marking element.

7. Device according to claim 6, further comprising a head support.

8. Device according to claim 7, wherein the signalers are distributed over the surface in a basically homogeneous density.

9. Device according to claim 8, wherein the signalers are arranged at approximately the same distance from each other.

10. Device according to claim 9, wherein the surface is developed in the shape of a spherical section.

11. Device according to claim 10, wherein the surface is basically developed in the shape of a hemisphere.

12. Device according to claim 7, wherein the support is arranged in such a manner that the head of the patient, while being supported on it, is basically positioned with the eyes at the center of the sphere.

13. Device according to claim 12, wherein the signalers are located on hyperbola lines.

14. Device according to claim 13, wherein that the signalers consist of, preferably, dot-shaped light sources for producing optical signals.

15. Device according to claim 14, wherein the light sources have different colors.

16. Device according to claim 13, wherein the signalers include sound transducers for the production of audible signals.

17. Device according to at least claim 16, further comprising a memory, which is coupled with the control mechanism, and in which an algorithm can be stored for the automatic activation of individual signalers or signaler groups.

18. Device according to claim 17, further comprising an input device that is coupled to the control mechanism and by which the signalers can optionally also be manually selected by the operator.

19. Device according to claim 18, wherein the control mechanism performs a statistical evaluation of the measuring results supplied by the time-determining device.

20. Device according to claim 19, further comprising a device, for the output of data, that is coupled to the control mechanism (20).

21. Device according to claim 20, wherein the intensity of the perceptual stimuli produced by the activated signaler can be adjusted by means of the control mechanism.

22. Device according to claim 21, wherein the start-signaling device emits an audible signal.

23. Device according to claim 22, wherein the distance of the signalers from the organs of perception of the patient, during the training with the device, is not smaller than the length of the patient's arm.

* * * * *